United States Patent [19]

Kubota et al.

[11] Patent Number: 4,895,966
[45] Date of Patent: Jan. 23, 1990

[54] POLYMERIZABLE ORGANOSILANE COMPOUND

[75] Inventors: Tohru Kubota; Toshinobu Ishihara; Mikio Endo, all of Niigata, Japan

[73] Assignee: Shin-Etsu Chemical Co., Ltd., Tokyo, Japan

[21] Appl. No.: 387,923

[22] Filed: Aug. 1, 1989

[30] Foreign Application Priority Data

Aug. 2, 1988 [JP] Japan .................... 63-193011

[51] Int. Cl.$^4$ .................... C07F 7/08; C07F 7/18
[52] U.S. Cl. .................... 556/448
[58] Field of Search .................... 556/448

[56] References Cited

U.S. PATENT DOCUMENTS

Re. 31,324 7/1983 Apotheker .................... 556/448 X

Primary Examiner—Paul F. Shaver
Attorney, Agent, or Firm—Millen, White & Zelano

[57] ABSTRACT

The organosilane compound of the invention is represented by the general formula

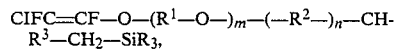

in which, for example, each $R^1$ is an ethylene group, $R^2$ is a methylene group, $R^3$ is a hydrogen atom, each R is an alkyl or alkoxy group, the subscript m is zero, 1, 2 or 3 and the subscript n is zero or 1. The terminal group of $ClFC=CF-O-$ has copolymerizability with conventional fluorine-containing polymerizable unsaturated compounds, e.g., tetrafluoroethylene, so that it is useful as a modifying agent of fluorine-containing polymers. A synthetic method for the compound is disclosed.

7 Claims, No Drawings

POLYMERIZABLE ORGANOSILANE COMPOUND

BACKGROUND OF THE INVENTION

The present invention relates to a novel organosilicon compound not known in the prior art nor described in any literatures. More particularly, the invention relates to a novel organosilane compound having an ethylenically unsaturated polymerizable group, of which the polymerizable group is a 1,2-difluoro-2-fluoroethenyl group bonded to the silicon atom through an ether linkage.

It is known that an organic compound having a 1,2-difluoro-2-chloroethenyloxy group of the formula $ClFC=CF-O-$ is copolymerizable with various kinds of fluorine-containing polymerizable olefinic compounds and is useful as a modifying agent of the polymers or copolymers derived from such a polymerizable fluorine-containing monomer to impart improved properties or specific functionality thereto. No organosilicon compound, however, is known in the prior art which has a 1,2-difluoro-2-chloroethenyloxy group and can be used for introducing an organosilicon moiety into fluorine-containing polymers along with the above mentioned effect of modification.

SUMMARY OF THE INVENTION

The present invention accordingly has an object to provide a novel organosilicon compound having a 1,2-difluoro-2-chloroethenyloxy group and useful as a comonomer in the polymerization of various kinds of fluorine-containing monomers.

Thus, the organosilicon compound of the present invention is an organosilane compound represented by the general formula $$ClFC=CF-O-(R^1-O-)_m-(-R^2-)_n-CHR^3-CH_2-SiR_3, \quad (I)$$

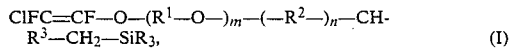

In which each $R^1$ is, independently from the others, an alkylene group having 1 to 10 carbon atoms, each $R^2$ is, independently from the others, an alkylene group having 1 to 10 carbon atoms, $R^3$ is a hydrogen atom or an alkyl group, each R is, independetly from the others, a monovalent hydrocarbon group, alkoxy group or triorganosiloxy group, the subscript m is zero, 1, 2 or 3 and the subscript n is zero or 1.

DETAILED DESCRIPTION OF THE PREFERRED EMBODIMENTS

In the above given general formula (I), the symbol $R^1$ denotes, each independently from the others, an alkylene group, which may be straightly linear or branched, having 1 to 10 carbon atoms exemplified, preferably, by ethylene and propylene groups. The symbol $R^2$ also denotes an alkylene group, which may be straightly linear or branched, having 1 to 10 carbon atoms but $R^2$ is preferably a methylene group, propylene group or heptamethylene group. $R^3$ is a hydrogen atom or an alkyl group such as methyl and ethyl groups. The group denoted by R is, each independently from the others, a monovalent hydrocarbon group free from aliphatic unsaturation exemplified by alkyl groups, e.g., methyl, ethyl and isopropyl groups, and aryl groups, e.g., phenyl and tolyl groups, alkoxy groups exemplified by methoxy and ethoxy groups and triorganosiloxy groups exemplified by trimethylsiloxy and triethylsiloxy groups. Preferably, the group denoted by R is a monovalent hydrocarbon group or an alkoxy group. The subscript m is zero, 1, 2 or 3 and n is zero or 1 so that the 1,2-difluoro-2-chloroethenyl group is bonded to the silicon atom through at least one ether linkage.

Typical, though not limitative, examples of the inventive polymerizable organosilane compound include:

(1,2-difluoro-2-chloroethenyloxy)ethyloxypropyl methyl diethoxy silane of the formula

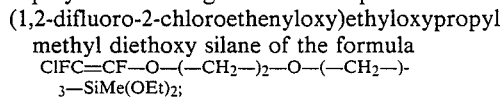
$ClFC=CF-O-(-CH_2-)_2-O-(-CH_2-)_3-SiMe(OEt)_2;$ (1,2-difluoro-2-chloroethenyloxy)ethyloxypropyl trimethoxy silane of the formula

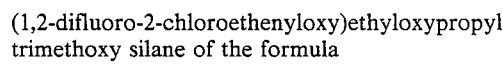
$ClFC=CF-O-(-CH_2-)_2-O-(-CH_2-)_3-Si(OMe)_3;$ (1,2-difluoro-2-chloroethenyloxy)propyl phenyl dimethoxy silane of the formula

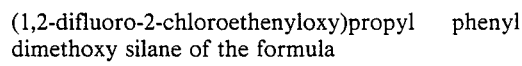
$ClFC=CF-O-(-CH_2-)_3-SiPh(OMe)_2;$ (1,2-difluoro-2-chloroethenyloxy)nonyl triethyl silane of the formula

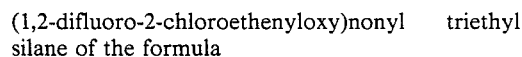
$ClFC=CF-O-(-CH_2-)_9-SiEt_3;$ and the like. The symbols of Me, Et and Ph in the above given formulas denote methyl, ethyl and phenyl groups, respectively.

The above defined organosilane compound of the present invention can be prepared, for example, by the following synthetic route. In the first place, chlorotrifluoroethylene of the formula $ClFC=CF_2$ is reacted with a sodium alcoholate compound represented by the general formula

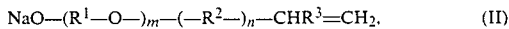
$$NaO-(R^1-O-)_m-(-R^2-)_n-CHR^3=CH_2. \quad (II)$$

in which each symbol has the same meaning as defined above, to form a compound having a 1,2-difluoro-2-chloroethenyloxy group and represented by the general formula

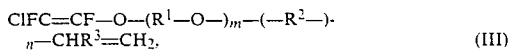
$$ClFC=CF-O-(R^1-O-)_m-(-R^2-)_n-CHR^3=CH_2. \quad (III)$$

in which each symbol has the same meaning as defined above, and this compound is then reacted with an organosilane compound of the formula

$$HSiR_3, \quad (IV)$$

in which R has the same meaning as defined above, to effect the hydrosilation reaction in the presence of a catalyst which is a compound of a noble metal or, in particular, platinum to give the desired organosilane compound of the invention represented by the general formula (I).

The alcoholate compound of the above given general formula (II) as the starting material of the synthetic process is exemplified by sodium allyl ethylene glycolate, sodium allyl diethylene glycolate, sodium 5-hexenyl alcoholate, sodium 8-nonenyl alcoholate and the like. The organosilane compound of the general formula (IV) is exemplified by triethyl silane, trimethoxy silane, methyl diethoxy silane, phenyl dimethoxy silane, tris(trimethylsiloxy) silane and the like.

In practicing the above described synthetic process, a reaction vessel equipped with a stirrer, thermometer, reflux condenser and gas inlet tube is charged with the sodium alcoholate compound of the formula (II) together with a solvent such as an aprotic solvent, e.g., toluene, xylene, hexane, tetrahydrofuran and the like, and chlorotrifluoroethylene is blown through the gas inlet tube into the reaction mixture in the vessel kept at a temperature of 30° to 70° C. The overall amount of the chlorotrifluoroethylene blown into the reaction mixture is at least equimolar to and up to twice by moles of the amount of the alcoholate compound. After completion of the reaction, the sodium salt precipitated in the reaction mixture is removed by washing with water and the organic solution is distilled to give the compound of the general formula (III). This compound of the formula (III) is introduced into a reaction vessel equipped with a stirrer, thermometer, reflux condenser and dropping funnel together with the catalytic compound, which is preferably chloroplatinic acid, and the organosilane compound of the formula (IV) is added dropwise to the reaction mixture in the vessel kept at 50° to 150° C. The amount of the organosilane compound of the formula (IV) is usually at least equimolar to but does not exceed 1.5 times by moles of the amount of the compound of the formula (III). After completion of the reaction, the reaction mixture is subjected to distillation to give the inventive organosilane compound of the general formula (I).

The organosilane compound of the present invention described above is copolymerizable with various kinds of conventional fluorine-containing ethylenically unsaturated polymerizable compounds such as tetrafluoroethylene, chlorotrifluoroethylene and the like so that the inventive compound is useful as a modifying or improving agent for the mechanical and thermal properties of the polymers obtained from these fluorine-containing monomers by the copolymerization therewith. When one or more of the groups denoted by R in the general formula (I) are hydrolyzable groups such as alkoxy groups, the copolymer of the inventive compound provides sites for crosslinking or chemical adsorption so that the fluorine-containing polymer can be imparted with crosslinkability by the reaction with atmospheric moisture or chemical adsorptivity to meet the requirements for various applications.

In the following, the organosilane compound of the present invention is described in more detail by way of examples.

EXAMPLE 1

Into a glass flask of 500 ml capacity equipped with a stirrer, reflux condenser, thermometer and gas inlet tube was introduced a toluene solution containing 0.5 mole of sodium allyl ethylene glycolate of the formula NaO—CH$_2$CH$_2$OCH$_2$CH=CH$_2$ dissolved in 300 ml of toluene, into which 0.5 mole of chlorotrifluoroethylene was introduced through the gas inlet tube at 40° to 50° C. over a period of 1 hour followed by standing of the mixture at the same temperature for 30 minutes. Thereafter, the reaction mixture was poured into 500 ml of water and the organic solution taken by phase separation was subjected to distillation under reduced pressure to give a fraction boiling at 80° to 85° C. under a pressure of 30 mmHg.

This fraction was introduced into a glass flask of 200 ml capacity equipped with a stirrer, reflux condenser, thermometer and dropping funnel together with 50 mg of chloroplatinic acid and 0.4 mole of trimethoxy silane was added dropwise through the dropping funnel into the mixture in the flask kept at 70° to 110° C. over a period of 1 hour followed by standing of the reaction mixture at 100° C. for 30 minutes to complete the reaction. The reaction mixture was then distilled under reduced pressure to give 103 g of a compound boiling at 109° to 112° C. under a pressure of 2 mmHg. This liquid product could be identified from the results of the mass spectrometric (MS) analysis, nuclear magnetic resonance absorption spectrometric (NMR) analysis and infrared absorption spectrophotometric (IR) analysis shown below to be an organosilane compound expressed by the formula

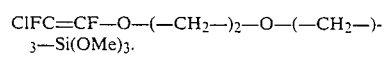

The above mentioned yield of the product was 64% of the theoretical value.

RESULTS OF ANALYSES

MS: m/z (relative intensity of peaks)
Electron-mpact method
289*(0.2); 163(9); 147(2); 121(100); 109(4); 91(38); 77(3); 61(4); 59(7); 45(3); 42(5)
(*accompanied by a peak assignable to the corresponding ion species with the $^{37}$Cl isotope)
Chemi-ionization method (with ammonia as the reactive gas)
321 (accompanied by a peak assignable to the corresponding ion species with the $^{37}$Cl isotope)
NMR: δ(ppm)

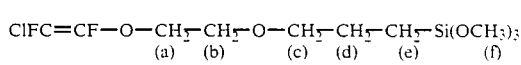

a: 3.92 to 4.14(m); b,c: 3.23 to 3.64(m); d: 1.37 to 1.84(m); e: 0.42 to 0.69(m); f: 3.43(s)
IR: cm$^{-1}$
2940; 2840; 1760; 1460; 1420; 1280; 1180; 1090; 1040; 910; 820

EXAMPLE 2

The experimental procedure was substantially the same as in Example 1 excepting replacement of the trimethoxy silane with the same molar amount of methyl diethoxy silane. Distillation of the final reaction mixture under reduced pressure gave 110 g of a product boiling at 98° to 101° C. under a pressure of 1.5 mmHg, which could be identified from the analytical results shown below to be an organosilane compound expressed by the formula

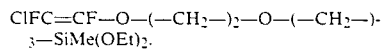

The above mentioned yield of the product was 66% of the theoretical value.

RESULTS OF ANALYSES

MS: m/z (relative intensity of peaks)
Electron-mpact method
287*(1); 175(7); 133(100); 105(10); 89(14); 77(19);

-continued

63(3); 61(6); 45(8); 42(5); 29(3)
(*accompanied by a peak assignable to the corresponding ion species with the $^{37}Cl$ isotope)
Chemi-ionization method (with ammonia as the reactive gas)
333 (accompanied by a peak assignable to the corresponding ion species with the $^{37}Cl$ isotope)
NMR: δ(ppm)

ClFC=CF—O—CH$_2$—CH$_2$—O—CH$_2$—CH$_2$—CH$_2$—Si(CH$_3$)(OCH$_2$CH$_3$)$_2$
     (a)    (b)      (c)    (d)     (e)     (f)   (g) (h)

a: 3.93 to 4.08(m); b,c,g: 3.19 to 3.89(m);
d: 1.31 to 1.79(m); e: 0.37 to 0.64(m); f: 0.01(s); h: 1.12(t)
IR: cm$^{-1}$
2960; 2880; 1760; 1440; 1400; 1260; 1180; 1100; 1080; 950

EXAMPLE 3

The reaction of a sodium alcoholate compound and chlorotrifluoroethylene was conducted in substantially the same manner as in Example 1 excepting replacement of the sodium allyl ethylene glycolate with the same molar amount of sodium 8-nonenyl alcoholate of the formula NaO(CH$_2$)$_7$CH=CH$_2$ to give a product boiling at 86° to 89° C. under a pressure of 7 mmHg by distillation under reduced pressure. This compound was reacted with trimethoxy silane in the same manner as in Example 1 to give 83 g of a product boiling at 136° to 138° C. under a pressure of 1 mmHg, which could be identified from the analytical results shown below to be an organosilane compound expressed by the formula ClFC=CF—O—(—CH$_2$—)$_9$—Si(OMe)$_3$.

The above mentioned yield of the product was 46% of the theoretical value.

RESULTS OF ANALYSES

MS: m/z (relative intensity of peaks)
Electron-mpact method
215(6); 131(3); 121(100); 91(16); 77(1); 61(2); 55(4); 43(2); 41(6); 29(4)
Chemi-ionization method (with ammonia as the reactive gas)
361 (accompanied by a peak assignable to the corresponding ion species with the $^{37}Cl$ isotope)
NMR: δ(ppm)

ClFC=CF—O—CH$_2$—(CH$_2$)$_7$—CH$_2$—Si(OCH$_3$)$_3$
     (a)    (b)     (c)     (d)

a: 3.85 to 4.08(m); b: 1.32 to 1.83(m);
c: 0.42 to 0.65(m); d: 3.46(s)
IR: cm$^{-1}$
2920; 2840; 1760; 1460; 1410; 1280; 1180; 1090; 1040;

-continued

900

What is claimed is:
1. An organosilane compound represented by the general formula

ClFC=CF—O—(R$^1$—O—)$_m$—(—$^2$—)$_n$—CH-R$^3$—CH$_2$—SiR$_3$, in which each R$^1$ is, independently from the others, an alkylene group having 1 to 10 carbon atoms, each R$^2$ is, independently from the others, an alkylene group having 1 to 10 carbon atoms, R$^3$ is a hydrogen atom or an alkyl group, each R is, independently from the others, a monovalent hydrocarbon group, alkoxy group or triorganosiloxy group, the subscript m is zero, 1, 2 or 3 and the subscript n is zero or 1.

2. The organosilane compound as claimed in claim 1 wherein the group denoted by R$^1$ is an ethylene group or propylene group.

3. The organosilane compound as claimed in claim 1 wherein the group denoted by R$^2$ is a methylene group, propylene group or heptamethylene group.

4. The organosilane compound as claimed in claim 1 wherein the group denoted by R$^3$ is a hydrogen atom.

5. The organosilane compound as claimed in claim 1 wherein the group denoted by R$^1$ is an ethylene group, the group denoted by R$^2$ is a methylene group, the group denoted by R$^3$ is a hydrogen atom, m is 1 and n is 1.

6. The organosilane compound as claimed in claim 1 wherein the group denoted by R$^2$ is heptamethylene group, the group denoted by R$^3$ is a hydrogen atom, m is zero and n is 1.

7. The organosilane compound as claimed in claim 1 wherein the group denoted by R is a monovalent hydrocarbon group or an alkoxy group.

* * * * *

UNITED STATES PATENT AND TRADEMARK OFFICE
CERTIFICATE OF CORRECTION

PATENT NO. : 4,895,966

DATED : January 23, 1990

INVENTOR(S) : TOHRU KUBOTA ET AL

It is certified that error appears in the above-identified patent and that said Letters Patent is hereby corrected as shown below:

Column 6, claim 1, formula:

reads "$ClFC=CF-O-(R^1-O-)m-(-^2-)n-CHR^3-CH_2-SiR_3,$"

should read --$ClFC=CF-O-(R^1-O-)m-(-R^2-)n-CHR^3-CH_2-SiR_3,$ --

Signed and Sealed this

Twenty-fifth Day of June, 1991

*Attest:*

HARRY F. MANBECK, JR.

*Attesting Officer*  Commissioner of Patents and Trademarks